United States Patent
Takahashi et al.

(10) Patent No.: US 6,462,239 B2
(45) Date of Patent: Oct. 8, 2002

(54) OXIDATION CATALYST AND OXIDATION PROCESS USING THE SAME

(75) Inventors: Ikuo Takahashi, Kobe; Hikaru Shibata, Himeji, both of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/832,104

(22) Filed: Apr. 11, 2001

(65) Prior Publication Data

US 2002/0007098 A1 Jan. 17, 2002

Related U.S. Application Data

(62) Division of application No. 09/323,225, filed on Jun. 1, 1999.

(30) Foreign Application Priority Data

Jun. 1, 1998 (JP) .......................................... 10-151643

(51) Int. Cl.$^7$ .......................... C07C 45/27; C07F 13/00
(52) U.S. Cl. .......................... 568/344; 568/338; 556/45
(58) Field of Search ............................ 556/45; 568/338, 568/344

(56) References Cited

FOREIGN PATENT DOCUMENTS

FR            A-2303785            3/1975

OTHER PUBLICATIONS

R.H. Bailes and M. Calvin "The oxygen–carrying synthetic chelate compounds. VII. Preparation", J. Am. Chem. Soc., Aug. 1947, vol. 69, pp. 1886–1893, XP000611957.

*Primary Examiner*—Sreeni Padmanabhan
(74) *Attorney, Agent, or Firm*—Birch, Stewart, Kolasch & Birch, LLP

(57) ABSTRACT

In the presence of (1) an oxidation catalyst comprising a crystalline complex of manganese with an N,N'-disalicylidenediamine (e.g. N,N'-disalicylidene $C_{2-8}$ alkylenediamines and N,N'-disalicylidene $C_{6-12}$ arylenediamines), or (2) an oxidation catalyst comprising the above complex and a basic nitrogen-containing compound, a substrate (e.g., β-isophorone or a derivative thereof) is oxidized with molecular oxygen to produce a corresponding oxide (e.g., ketoisophorone). Ketoisophorone can be obtained from β-isophorone with high conversion and high selectivity.

18 Claims, No Drawings

OXIDATION CATALYST AND OXIDATION PROCESS USING THE SAME

This application is a divisional of co-pending application No. 09/323,225, filed on Jun. 1, 1999, the entire contents of which are hereby incorporated by reference and for which priority is claimed under 35 U.S.C. § 120; and this application claims priority of application No. 10-151643 filed in Japan on Jun. 1, 1998 under 35 U.S.C. § 119.

FIELD OF THE INVENTION

The present invention relates to an oxidation catalyst, an oxidation process using the same, and a process for producing ketoisophorone from β-isophorone.

BACKGROUND OF THE INVENTION

Ketoisophorone (4-oxoisophorone), a useful intermediate for a starting material of medicines, perfumes, condiments, and for polymer, is produced from isophorone and the like. For example, as a process for producing 4-oxoisophorone by oxidizing β-isophorone with oxygen, there have been proposed a method in which β-isophorone is oxidized with oxygen in the presence of a phosphomolybdic acid or a silicomolybdic acid [Japanese Patent Publication No. 30696/1980 (JP-B-55-30696)], a method in which β-isophorone is oxidized with oxygen in the coexistance of a phosphomolybdic acid or a silicomolybdic acid and an alkaline metal compound or an aromatic amine [Japanese Patent Application Laid-Open No.191645/1986 (JP-A-61-191645)], and a method in which β-isophorone is oxidized with oxygen in the presence of a vanadium catalyst [Japanese Patent Application Laid-Open No. 93947/1975 (JP-A-50-93947)]. Japanese Patent Application Laid-Open No. 81347/1974 (JP-A-49-81347) discloses a method for producing 4-oxoisophorone by oxidizing β-isophorone with an alkaline metal chromic acid salt or a dichromate or a chromium trioxide. In the Chem. Lett. (1983), (7), 1081, there is disclosed a method for producing 4-oxoisophorone by oxidizing β-isophorone using t-butylhydroperoxide in the presence of a palladium catalyst. However, in these methods, the selectivity of ketoisophorone is reduced, therefore separation of the formed by-product(s) or a metal catalyst and purification of the object compound are complicated. Moreover, these methods involve using a heavy metal compound requiring special treatment, such as chromium, or a peroxide needed to be handled with care, which results in a decrease in working efficiency.

Moreover, as a method for producing ketoisophorone from β-isophorone, Japanese Patent Application Laid-Open No. 125316 (JP-A-51-125316) discloses a method for producing an ethylenically unsaturated dicarboxylic acid by oxidizing β-ethylenically unsaturated ketone with molecular oxygen or a molecular oxygen-containing gas in the presence of an inorganic base or an organic base and a cobalt or manganese chelate. In this method, however, the yield of ketoisophorone is low due to the use of a straight-chain secondary or tertiary amine such as triethylamine as the organic base.

In Japanese Patent Application Laid-Open No. 53553/1998 (JP-A-10-53553) discloses a method for producing ketoisophorone by oxidizing β-isophorone with molecular oxygen in the presence of bis(2-hydroxybenzylidene)-ethylenediamine-manganese complex salt (i.e., manganese-salene), an organic base, a specific substance having a catalytic action (e.g., acetylacetone), and water. In the literature, there is recited as the manganese complex salt a complex in which 1 mole of bis(2-hydroxybenzylidene)-ethylenediamine is coordinated relative to 1 mole of manganese. However, even in the above method using the above manganese complex salt, the conversion and the selectivity of a substrate are not improved enough. Particularly, a higher concentration of β-isophorone in the reaction system causes a considerable decrease in the yield of ketoisophorone. For example, when the concentration of β-isophorone is 20% by weight or more, the conversion and/or the selectivity is decreased to a large extent. Therefore, relatively large amounts of a manganese complex salt and an organic base are required for an improved conversion. Further, a lower concentration of oxygen remarkably decreases the reaction rate.

SUMMARY OF THE INVENTION

Thus, an object of the present invention is to provide an oxidation catalyst capable of oxidizing a substrate with high conversion and high selectivity regardless of the concentration of the substrate, and an oxidation process using the same.

Another object of the present invention is to provide an oxidation catalyst capable of oxidizing a substrate with high conversion and high selectivity even used in a catalytic amount, and an oxidation process using the same.

Further object of the present invention is to provide an oxidation catalyst which ensures the efficient proceeding of an oxidative reaction efficiently proceeds even with, as a source of molecular oxygen, a low oxygen content gas, such as air, and an oxidation process using the same.

Still further object of the present invention is to provide an oxidation catalyst capable of producing ketoisophorone with maintaining high conversion and high selectivity even with a high β-isophorone concentration and a low oxygen concentration, and a process for producing ketoisophorone using the same.

The inventors of the present invention did intensive investigations to achieve the above objects and found that, even in a reaction system with a high substrate (e.g., β-isophorone) concentration and a low oxygen concentration, the substrate can be oxidized with high conversion and high selectivity by using a specific complex comprising manganese and an N,N'-disalicylidenediamine, and that the conversion and the selectivity are remarkably improved by further employing or incorporating a basic nitrogen-containing compound in combination with the above complex. The present invention was accomplished based on the above findings.

Accordingly, the oxidation catalyst of the present invention comprise (1) a crystalline complex of manganese with an N,N'-disalicylidenediamine, or (2) the above complex (1) and a basic nitrogen-containing compound. The melting point of the above crystalline complex may be about 190 to 240° C.

The present invention further includes an oxidation process in which a substrate is oxidized with oxygen in the presence of the above oxidation catalyst, for example, a process which comprises oxidizing β-isophorone or a derivative thereof with molecular oxygen to produce a corresponding ketoisophorone or a derivative thereof.

In the specification, the term "N,N'-salicylidenediamine" is taken to mean that an N,N'-salicylidenediamine may have a structure in which a salicylidene group is bound to a nitrogen atom of each amino group of an aliphatic, alicyclic, or aromatic diamine.

DETAILED DESCRIPTION OF THE INVENTION

Complex

A complex of the oxidation catalyst of the present invention is crystalline and comprising manganese and an N,N'-disalicylidenediamine. The valence of manganese is usually in the range of divalent to tetravalent (particularly, divalent). In addition to manganese, the complex may further comprise other transition metal component, if needed, for example, a transition metal element of the Groups 3 to 12 of the Periodic Table of the Elements [e.g., the group 5 elements (e.g., V, Nb), the group 6 elements (e.g., Cr), the group 7 elements (e.g., Re), the group 8 elements (e.g., Fe, Ru), the group 9 elements (e.g., Co, Rh), the group 10 elements (e.g., Ni, Pd) and the group 11 elements (e.g., Cu)].

The above N,N'-disalicylidenediamine has a structure in which a salicylidene group is bound to each nitrogen atom of the two amino groups of an aliphatic, alicyclic, or aromatic diamine. The manganese complex of the present invention comprising manganese and an N,N'-disalicylidenediamine ligand is represented by the following formula:

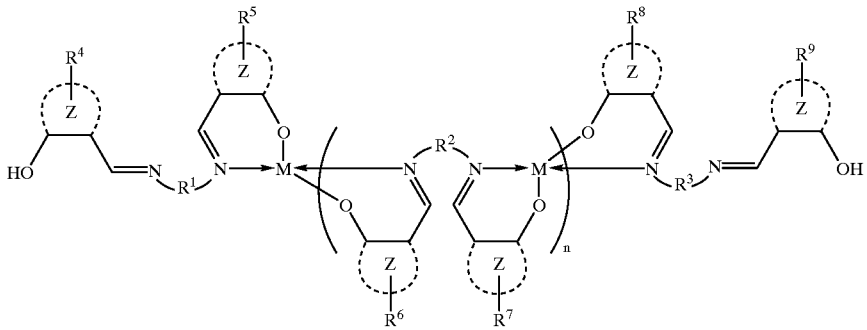

wherein $R^1$, $R^2$, and $R^3$ are the same or different and each represents an alkylene group, a cycloalkylene group, or an arylene group and may have a substituent; $R^4$ to $R^9$ are the same or different and each represents hydrogen atom, a halogen atom, an alkyl group, a hydroxyl group, a hydroxymethyl group, or an alkoxy group; the rings Z are aromatic rings; M stands for manganese; and n is 0 or an integer of not less than 1.

As a diamine corresponding to the above $R^1$, $R^2$, and $R^3$, there may be exemplified aliphatic diamines such as a straight- or branched chain $C_{2-10}$ alkylenediamines and a $C_{2-10}$ alkylenediamine containing an imino group (NH group); alicyclic diamines such as a diaminocyclohexane; and $C_{6-12}$ aromatic diamines such as a diaminobenzene, a diaminonaphthalene, a biphenyldiamine and derivatives thereof.

Examples of the N,N'-disalicylidenediamine are N,N'-disalicylidene $C_{2-8}$ alkylenediamines such as N,N'-disalicylidene ethylenediamine, N,N'-disalicylidene trimethylenediamine, and N,N'-disalicylidene-4-aza-1,7-heptanediamine (preferably, N,N'-disalicylidene $C_{2-5}$ alkylenediamine); and N,N'-disalicylidene $C_{6-12}$ arylenediamines such as N,N'-disalicylidene-o-phenylenediamine, and N,N'-disalicylidene-2,2'-biphenylenediamine. Examples of the particularly preferred N,N'-disalicylidenediamine are N,N'-disalicylidene $C_{2-4}$ alkylenediamines such as N,N'-disalicylidene ethylenediamine and N,N'-disalicylidene trimethylenediamine.

As the aromatic rings Z, there may be exemplified hydrocarbon rings (e.g., benzene, naphthalene) and heterocycles (e.g., nitrogen atom-containing heterocycles such as pyridine, pyrazine, pyrimidine, and quinoline; sulfur atom-containing heterocycles such as thiophene; and oxygen atom-containing heterocycles such as furan). As to the substituents $R^4$ and $R^9$ of the aromatic rings Z, examples of the halogen atom are bromine, chlorine, and fluorine, and examples of the alkyl group are $C_{1-6}$ alkyl groups such as methyl, ethyl, propyl, butyl, and t-butyl group. Examples of the alkoxy group are $C_{1-6}$ alkoxy groups such as methoxy, ethoxy, propoxy, and butoxy groups. The substituents $R^4$ and $R^9$ are usually hydrogen atoms, $C_{1-4}$ alkyl groups, or hydroxymethyl groups.

In the complex shown by the above formula, n is 0 or an integer of not less than 1 (e.g., 1 to 5, particularly 1 or 2).

In the above complex, m+1 mole of the N,N'-disalicylidenediamine is coordinated to m mole of manganese (m is an integer of not less than 1), and thus the complex is structurally different from a conventional manganese complex in which 1 mole of the N,N'-disalicylidenediamine is coordinated to 1 mole of manganese. Moreover, in contrast to the conventional manganese complex being noncrystalline (amorphous), the complex of the present invention is crystalline and shows a clear melting point in accordance with a thermal analysis by TC/TDA. The melting point of the complex is usually about 190 to 240° C. and particularly about 200 to 220° C. Moreover, the complex of the present invention can be distinguished from conventional manganese complexes by whether there is an absorption peak for the hydroxyl group in the infrared absorption spectrum or not.

An oxidation catalyst comprising such complex is useful for producing an oxide (e.g., ketoisophorone or derivatives thereof) by oxidizing a substrate (e.g., β-isophorone or a derivative thereof) with molecular oxygen. Moreover, the oxidation catalyst may comprise the above complex and a basic nitrogen-containing compound.

Production Process of Complex

The above complex can be obtained by coordinating an excess amount of an N,N'-disalicylidenediamine with a manganese compound. As the manganese compound, there may be exemplified organic acid salts (e.g., acetates), halides (e.g., manganese chloride), and inorganic acid salts. The proportion of the N,N'-disalicylidenediamine relative to the manganese compound is about 0.5 to 5, preferably about 0.9 to 3, and particularly about 1 to 2 (molar ratio). Even if the proportions are almost equimolar with each other, a complex in which a substantially excess mole of an N,N'-disalicylidenediamine is coordinated can be obtained by liberating or separating a manganese compound though deteriorated in yield.

The reaction may be conducted in an inert solvent (e.g., an organic solvent such as an alcohol). Practically, the reaction is carried out in an atmosphere of an inert gas and can be effected usually with stirring at a temperature within the range of 70° C. to a reflux temperature of a solvent. The complex can be obtained by recovering or collecting the reaction product and, if needed, purifying by a recrystallization technique, and drying.

Basic Nitrogen-containing Compound

A combination of the above complex and the basic nitrogen-containing compound gives an oxidation catalyst having a higher activity and remarkably improves the conversion of the substrate (e.g., β-isophorone) and the selectivity of the object oxide (e.g., ketoisophorone).

The basic nitrogen-containing compound includes not only aliphatic amines but also cyclic bases (alicyclic or aromatic amines), and the cyclic bases may be heterocyclic amines. The amines may be primary, secondary, or tertiary, and a tertiary amine is usually employed.

Examples of the aliphatic amines are mono-, di-, or tri-$C_{1-6}$ alkylamines such as dimethylamine, diethylamine, dibutylamine, triethylamine, and tributylamine; alkanolamines such as ethanolamine, diethanolamine, and triethanolamine; alkylenediamines such as ethylenediamine, diethylenetriamine and butanediamine or N-substituted compounds of the alkylenediamines.

As the cyclic bases, there may be mentioned, for example, alicyclic or aromatic bases having at least one nitrogen atom. The alicyclic bases include alicyclic hydrocarbons having an amino group or an N-substituted amino group (alicyclic amines), and compounds in which at least one nitrogen atom constitutes a hetero atom of the ring (nitrogen-containing heterocyclic compounds). Examples of the alicyclic amines include cycloalkylamines or derivatives thereof (mono-or di-$C_{1-4}$ alkylaminocycloalkanes such as dimethylaminocyclohexane). The nitrogen-containing heterocyclic compounds includes, for example, 5- to 10-membered mono- and heterocyclic compounds such as pyrrolidine or its derivatives [N-substituted pyrrolidines (e.g., N-$C_{1-4}$ alkylpyrrolidines such as N-methylpyrrolidine), substituted pyrrolidines (e.g., 2- or 3-methylpyrrolidine, 2- or 3-aminopyrrolidine), or the like]; piperidine or its derivatives [N-substituted piperidines (e.g., N-$C_{1-4}$ alkylpiperidine such as N-methylpiperidine; piperylhydrazine), substituted piperidines (o-aminopiperidine, m-aminopiperidine, and p-aminopiperidine)]; alkylene imines or its derivatives [hexamethylene imine, N-substituted hexamethylene imines (e.g., N-methylhexamethylene imine)]; piperazine or its derivatives [N-$C_{1-4}$ alkylpiperazines such as N-methylpiperazine; N,N'-di-$C_{1-4}$ alkylpiperazines such as N,N'-dimethylpiperazine; 2-methylpiperazine]; and poly- and heterocyclic compounds such as azabicyclo $C_{7-12}$ alkanes (e.g., quinuclidine, 1,4-diazabicyclo[2.2.2]octane (DABCO), 1,5-diazabicyclo[3.2.1]octane, 1,5-diazabicyclo [3.3.0]octane, 1,4-diazabicyclo[4.2.0]octane, 1,5-diazabicyclo [3.3.1]nonane, 1,5-diazabicyclo[5.3.0]decane), azatricyclo $C_{8-16}$ alkanes (e.g., 1,5-diazatricyclo[3.3.0.0$^{2,6}$] octane, hexamethylenetetramine), and derivatives thereof.

Among these alicyclic bases, those containing at least one (particularly, 2)(e.g., 2 to 6) nitrogen atom are preferable (particularly, the above alicyclic bases having a nitrogen atom as a hetero atom), and examples of such alicyclic bases are 6 to 8-membered mono- and heterocylcic compounds (e.g., piperazine, N-substituted piperazines, amino group-substituted piperazines); azabicyclo $C_{7-10}$ alkanes (e.g., quinuclidine, DABCO, or its derivatives); and hexamethylenetetramine.

The aromatic bases includes aromatic hydrocarbons having an amino group or an N-substituted amino group or both (aromatic amines), and aromatic compounds in which at least one nitrogen atom constitutes a hetero atom of a ring (aromatic heterocyclic compounds). Examples of the aromatic amines are aniline or derivatives thereof (e.g., N,N'-di-$C_{1-4}$ alkylanilines); toluidine or derivatives thereof (e.g., N,N'-di-$C_{1-4}$ alkyltoluidines); and anisidine or derivatives thereof (e.g., N,N'-di-$C_{1-4}$ alkylanisidines). As the aromatic heterocyclic compound, an aromatic compound having at least two nitrogen atoms in which at least one nitrogen atom constitutes a ring is preferable. An examples of such aromatic heterocyclic compound is a compound having a substituent containing at least a nitrogen atom (e.g., amino group, N-substituted amino group) on an aromatic heterocyclic compound having at least one nitrogen atom as a hetero atom (e.g., pyridine) [e.g., 2-, 3-, or 4-aminopyridine, 2-, 3-, or 4-mono or dialkylaminopyridines (e.g., di-$C_{1-4}$ alkylaminopyridines such as dimethylaminopyridine), 2-, 3-, or 4-piperidinopyridine, and 4-pyrrolidinopyridine]; pyrazine or its derivatives (e.g., 2-methylpyrazine); phthalazine, quinazoline, quinoxaline, or derivatives thereof; phenanthroline or its derivatives (e.g., 1,10-phenanthroline); and 2,2-bipyridyl or its derivatives. N,N-dialkylaminopyridines, pyrazine, phenanthroline, or derivatives thereof are particularly preferred.

In the above cyclic base, another nitrogen atom(s) than the one constituting a ring comprises preferably a tertiary amino group, and the nitrogen atom constituting the ring may have a substituent other than a hydrogen atom (e.g., a $C_{1-4}$ alkyl group). The basic nitrogen-containing compound can be used either singly or as a combination of two or more species.

The proportion of the basic nitrogen-containing compound relative to the above complex (the former/the latter) can suitably be selected from the range of about 0.1/1 to 500/1 (molar ratio) and preferably about 0.5/1 to 250/1 (e.g., 0.8/1 to 250/1).

Oxidation Reaction

By oxidizing a substrate with molecular oxygen using the oxidation catalyst of the present invention, the corresponding oxide can be produced in high yield even if the concentration of the substrate in a reaction system is high. Moreover, its high activity permits a remarkable decrease in the amount of the oxidation catalyst as compared to conventional manganese complexes, and therefore an oxide can be produced with high conversion and high selectivity even in the presence of an exceedingly minute amount of the oxidation catalyst. Further, since the oxide can be produced with high conversion and high selectivity even if the concentration of oxygen is low, air or the like can also be used as an oxygen source.

Amount of Catalyst

The amount of the oxidation catalyst to be used is, for example, about 0.001 to 5 parts by weight, preferably about 0.01 to 1 part by weight, and more preferably about 0.05 to 0.5 part by weight, relative to 100 parts by weight of β-isophorone or a derivative thereof. The amount of each constituent of the oxidation catalytic system relative to 1 mole of β-isophorone or a derivative thereof is as follows.

Complex: about $1 \times 10^{-5}$ to $1 \times 10^{-2}$ mole (preferably, about $1 \times 10^{-2}$ to 0.5 mole)

Basic nitrogen-containing compound: about $5 \times 10^{-2}$ to 1 mole (preferably, about $1 \times 10^{-2}$ to 0.5 mole).

Substrate

The species of the above-mentioned substrate is not particularly limited, and there may be exemplified β-isophorone (3,5,5-trimethylhex-3-ene-1-one) or derivatives thereof and compounds having a structure similar to that of β-isophorone, for example, compounds having a 3-cyclohexenone skeleton. Particularly, the oxidation catalyst of the present invention is useful in producing the corresponding ketoisophorone by oxidizing β-isophorone or a derivative thereof with molecular oxygen.

The concentration of the substrate in the reaction system is not particularly restricted, and the object compound can be produced with high conversion and high selectivity even at a concentration of, e.g., about 5 to 50% by weight. Particularly, even if the concentration of the substrate (e.g., □-isophorone or a derivative thereof) is 10 to 50% by weight and preferably 20 to 50% by weight, the oxidative reaction can be effected with retaining or maintaining a selectivity of 90% or higher (e.g., a selectivity of about 93 to 97%), and therefore, the oxidation and the catalyst of the present invention has great advantages and is remarkably useful in view of industry.

In the present invention, in addition to oxygen and oxygen-containing gases, a compound generating molecular oxygen is also employed as an oxygen source so far as capable of providing molecular oxygen. As the oxygen source, highly pure oxygen or a high oxygen content gas may be used, the oxygen gas diluted with an inert gas, e.g., nitrogen, helium, argon, or carbon dioxide is preferably supplied to the reaction system. Moreover, with the oxidation catalytic systems of the present invention, the substrate can be oxidized effectively even with air instead of oxygen as the oxygen source. The use of air as the oxygen source is not only highly advantageous in view of economics but also reduces the danger of explosions encountered in industrialization.

The oxygen concentration of the oxygen source is, for example, about 5 to 100% by volume, preferably about 5 to 50% by volume, and particularly about 7 to 30% by volume. Even at such a low oxygen concentration as of about 8 to 25% by volume, the oxidative reaction effectively proceeds.

When supplying molecular oxygen to a reaction vessel or container, the reaction may be carried out in a closed system with enough molecular oxygen previously supplied, or may be conducted in a continuous stream of molecular oxygen. In the case of a stream of molecular oxygen, the flow rate is, for example, about 0.1 to 10L/min and preferably about 0.5 to 5L/min per unit volume (1L) of the vessel.

The oxidative reaction may be either gas-phase oxidation or liquid-phase oxidation. The reaction may be conducted in the absence of a solvent, and usually carried out in an inert solvent.

As the reaction solvent, hydrophilic solvents or hydrophobic solvents such as hydrocarbons, halogenated hydrocarbons, esters, ketones, ethers and aprotic polar solvents may be used provided that they do not impair the oxidative reaction. Since water is produced in the oxidative reaction, some species of basic nitrogen-containing compound are difficult to recover and sometimes the solvent can not be recycled. In such case, a water-insoluble (or hydrophobic) organic solvent is preferable. Examples of the water-insoluble organic solvent are aliphatic hydrocarbons solvents such as hexane, heptane, and octane; aromatic hydrocarbon such as benzene, toluene, and xylene; alicyclic hydrocarbons such as cyclohexane; ketones (particularly, dialkyl ketones) such as methyl ethyl ketone and dibutyl ketones (e.g., diisobutyl ketone, di-t-butyl ketone); ethers such as diethyl ether, diisopropyl ether, dibutyl ether, tetrahydrofuran, dioxane, ethylene glycol monomethyl ether, ethylene glycol dimethyl ether, diethylene glycol monomethyl ether, and diethylene glycol dimethyl ether; halogen-containing solvents such as monochloroethane, dichloroethane, chloroform, carbon tetrachloride, and 1,2-dichloroethane; and esters such as methyl acetate, ethyl acetate, and butyl acetate. Dialkyl ketones are preferable, and dibutyl ketones are particularly preferred.

The amount of the solvent to be used is not particularly restricted and may be selected from within the range of about 5 to 70% by weight and preferably about 15 to 60% by weight (e.g., 20 to 55% by weight).

The proportion of the water content in the reaction system can be selected from within the range not adversely affecting on the reaction such as inactivation of the catalytic system, and is about 1% by weight or less (about 0.001 to 1% by weight) and preferably about 0.5% by weight or less (about 0.001 to 0.5% by weight). Despite acceleration of the reaction at the initial stage, the water content exceeding 1% by weight results in a subsequent cessation of the reaction or a decrease in selectivity. The water in the reaction system includes not only the water contained at the beginning or initial stage of the reaction but also the water produced by the reaction. In the present reaction system, there is usually present a finite amount of water. It is desirable that the water produced by the reaction is removed from the system. The amount of the produced water varies with the concentration of β-isophorone substrate, and the amount of the water to be removed is at least about 30% by weight, preferably at least about 50% by weight, and more preferably at least about 80% by weight, relative to the total amount of the water produced.

The reaction temperature can be selected from within the range of, e.g., about 10 to 100° C. (preferably about 20 to 60° C.) according to the reaction rate, selectivity, and the solvent to be used. The reaction can be conducted either at atmospheric pressure or under applied pressure [to about 150 atm ($152 \times 10^5$ Pa)] and preferably at atmospheric pressure. The reaction time (or residence time) is not particularly restricted and can be selected from within the range of about 10 seconds to 24 hours, depending upon the system of the reaction (e.g., a continuous system or a batch system).

The reaction can be carried out in a conventional system such as a batch system, a semi-batch system, or a continuous system. In the continuous system, portions of the catalyst are continuously or intermittently removed from a reactor for regeneration, and the regenerated catalyst (i.e., a complex of a transition metal with an N,N'-disalicylidenediamine) may be recycled to the reactor to be reused. In the batch system, the catalyst or the constituents of the catalyst may be separated and recovered from a reaction product after completion of the reaction, wholly or partially regenerated and may be reused repeatedly as a catalyst for the reaction.

An oxide produced by the reaction (e.g., ketoisophorone) can easily be separated and purified with a conventional separation technique such as filtration, condensation, distillation, extraction, crystallization, recrystallization and column chromatography, or a combination thereof. Particularly, according to the present invention, the conversion of β-isophorone and the selectivity of ketoisophorone can be significantly improved, and the production of by-product(s) is remarkably inhibited. Therefore, even though the separation and purification step is required of ketoisophorone, ketoisophorone can be separated and purified with easiness and efficiency, and therefore need not be highly separation-purified.

According to the present invention, the substrate can be oxidized with high conversion and high selectivity regardless of its concentration by using the crystalline manganese complex of manganese with the N,N'-disalicylidenediamine. Moreover, even if the amount of the catalyst is extremely minute, the substrate can be oxidized with high conversion and high selectivity. Further, even when the oxygen concentration of the molecular oxygen source is low as in the case of air, the oxidation catalyst of the present invention proceeds efficiently an oxidative reaction. Therefore, when the catalyst of the present invention is applied to the oxidation of β-isophorone, even if the concentration of β-isophorone is high and the oxygen concentration is low, ketoisophorone can be produced with retaining high conversion and selectivity. Particularly, even in the reaction system with a high β-isophorone concentration, it is possible to maintain high selectivity and produce ketoisophorone with an improved efficiency.

EXAMPLES

The following examples are intended to show the present invention in further detail and should be no means be construed as defining the scope of the invention.

The substrate, transition metal complex, nitrogen-containing compounds, and the solvent used in Examples and Comparative Examples are as follows.

1. Substrate: β-isophorone (β-IP)

2. Manganese complex (b-1): crystalline manganese complex

A reactor was fed with 169 g (630 mmol) of the N,N'-disalicylideneethylenediamin (EDSA) and 5,000 ml of methanol, and the EDSA was dissolved at a reflux temperature under a nitrogen stream. According to the method recited in Inorg. Synth. 3 (1950) 196, N,N'-disalicylideneethylenediamine (EDSA) had been synthesized by refluxing 2 mol of salicylaldehyde and 1 mol of ethylenediamine in ethanol for 6 hours.

A solution of 156 g (637 mmol) of manganese acetate·tetrahydrate Mn $(OAc)_2 \cdot 4H_2O$ and 1,500 ml of methanol was added to the above-described solution of EDSA in methanol at 50° C. in a nitrogen stream, and the mixture was reacted at a reflux temperature in a nitrogen stream for 8 hours. After the completion of the reaction, the mixture was allowed to stand overnight in an atmosphere of nitrogen to be cooled, and stored in a container (or vessel) in which a nitrogen gas is flowing. With a nitrogen gas flowing through the container, the mixture was filtered and dried in vacuo at 80° C. for 6 hours to obtain 135.4 g of crystals (yield: 70%).

Thermal analysis (TC/TDA) of the crystalline complex showed the melting point of 207.8° C.

| | Elemental analysis |
|---|---|
| Found | C: 65.5, H: 5.2, N: 9.5 |
| Calculated | C: 65.2, H: 5.1, N: 9.5 (corresponding to the above formula in which n = 0) |
| Calculated | C: 63.3, H: 4.9, N: 9.2 (corresponding to the above formula in which n = 0) |

A manganese complex was obtained according to the method recited in the J. Am. Chem. Soc., 108 (1986) 2317. In other words, to a mixed solution of 2.15 g (8 mmol) of EDSA and 50 ml of methanol was added a solution of 0.90 g (16 mmol) of potassium hydroxide and 20 ml of methanol. Thereafter, to the resultant mixture was added a solution of 1.98 g (8.08 mmol) of manganese acetate·tetrahydrate Mn $(OAc)_2 \cdot 4H_2O$ and 30 ml of methanol in a nitrogen stream, and the reaction mixture was refluxed at a reflux temperature for 5 hours. Thereafter, the reaction mixture was cooled to room temperatures taking 2 hours, and then filtered. The cake or residue was washed with 10 ml of methanol, and filtered, and dried in vacuo at 100° C. for 8 hours to obtain a manganese complex.

Thermal analysis (TC/TDA) of the manganese complex showed no clear endoergic peak and revealed the complex to be noncrystalline (amorphous). The melting point of the sole EDSA was 127.6° C.

| | Elemental analysis |
|---|---|
| Found | C: 59.6, H: 4.3, N: 8.7 |
| Calculated | C: 59.8, H: 4.4, N: 8.7 |

3. Nitrogen-containing compound (c-1): 1,4-diazabicyclo[2.2.2]octane (DABCO)
(c-2): 4-dimethylaminopyridine
(c-3): 2-dimethylaminopyridine
(c-4): 1,10-phenanthroline
(c-5): triethylamine 4. Solvent: diisobutyl ketone Examples 1 to 8 and Comparative Examples 1 to 3

An 1L glass reactor equipped with a mechanical stirrer with turbine blades and a molecular oxygen gas inlet tube having a porous glass unit was fed with β-isophorone, a manganese complex, a nitrogen-containing compound, and the solvent in proportions shown in Table 1, and the reaction was carried out with an oxygen-containing gas (oxygen concentration, volume%) flowing at a constant flow rate.

The conversions of β-isophorone and the selectivities of ketoisophorone from β-isophorone in Examples 1 to 8 and Comparative Examples 1 to 3 are shown in Table 1 with the reaction conditions.

TABLE 1

| | Amount of β-IP (concentration wt %) | Mn Complex Amount of Mn complex (mmol) | Nitrogen-containing compound Species | Amount | Amount of Solvent |
|---|---|---|---|---|---|
| Example 1 | 133 g (23.7) | b-1 0.24 g (0.41) | c-1 | 8.5 g | 420 g |
| Example 2 | 250 g (43.1) | b-1 0.32 g (0.54) | c-1 | 10.0 g | 320 g |
| Example 3 | 250 g (42.9) | b-1 0.32 g (0.54) | c-2 | 12.2 g | 320 g |
| Example 4 | 200 g (34.4) | b-1 0.28 g (0.47) | c-3 | 12.2 g | 370 g |
| Example 5 | 300 g (53.6) | b-1 0.36 g (0.61) | c-1 | 10.0 g | 250 g |
| Example 6 | 200 g (34.4) | b-1 0.28 g (0.47) | c-1 | 12.0 g | 370 g |

TABLE 1-continued

| | Oxygen-containing gas | | | | | |
| --- | --- | --- | --- | --- | --- | --- |
| | Flow rate (L/min) | Oxygen concentration (volume %) | Reaction Temperature (° C.) | Reaction Time (hr) | Conversion (%) | Selectivity (%) |
| Example 1 | 1.4 | 21 | 40 | 4 | 99 | 95 |
| Example 2 | 1.8 | 21 | 40 | 4 | 98 | 93 |
| Example 3 | 1.8 | 21 | 40 | 4 | 98 | 90 |
| Example 4 | 1.7 | 21 | 40 | 4 | 99 | 91 |
| Example 5 | 2.0 | 21 | 45 | 4 | 98 | 88 |
| Example 6 | 2.5 | 10 | 40 | 5 | 98 | 95 |

TABLE 2

| | Amount of β-IP (concentration wt %) | Mn complex Amount of Mn complex (mmol) | Nitrogen-containing compound | | Amount of Solvent |
| --- | --- | --- | --- | --- | --- |
| | | | Species | Amount | |
| Example 7 | 250 g (43.1) | b-1 0.32 g (0.54) | c-4 | 9.5 g | 320 g |
| Example 8 | 133 g (23.7) | b-1 0.32 g (0.41) | c-1 | 8.5 g | 420 g |
| Comp. Ex.1 | 200 g (31.8) | b-2 0.28 g (0.75) | c-5 | 18.0 g | 410 g |
| Comp. Ex.2 | 200 g (34.4) | b-2 0.28 g 0.75 | c-1 | 12.0 g | 370 g |
| Comp. Ex.3 | 250 g (44.2) | b-2 0.32 g (1.00) | c-5 | 26.0 g | 290 g |

TABLE 2-continued

| | Oxygen-containing gas | | | | | |
| --- | --- | --- | --- | --- | --- | --- |
| | Flow rate (L/min) | Oxygen concentration (volume %) | Reaction Temperature (° C.) | Reaction Time (hr) | Conversion (%) | Selectivity (%) |
| Example 7 | 1.5 | 21 | 35 | 6 | 99 | 92 |
| Example 8 | 1.2 | 21 | 40 | 5 | 99 | 93 |
| Comp. Ex.1 | 1.4 | 21 | 40 | 4 | 21 | 80 |
| Comp. Ex.2 | 1.5 | 21 | 40 | 4 | 87 | 90 |
| Comp. Ex.3 | 1.0 | 100 | 40 | 4 | 85 | 71 |

As obvious from Tables 1 and 2, even if the concentration of β-isophorone is high and the oxygen concentration is low, the conversion and selectivity can be largely improved in Examples as compared with Comparative Examples. Moreover, the conversion and selectivity can be further improved by incorporating a nitrogen-containing compound. Further, even if the concentration of a manganese complex is small, ketoisophorone can be formed with high activities.

What is claimed is:

1. An oxidation process that comprises the step of oxidizing a substrate with oxygen in the presence of an oxidation catalyst comprising a crystalline complex of manganese with an N,N'-disalicylidenediamine, wherein, in said complex, m+1 moles of the N,N'-disalicylidenediamine is coordinated to m moles of the manganese and m is an integer of not less than 1, and wherein the infrared spectrum of the complex indicates an absorption peak for the hydroxyl group.

2. The oxidation process of claim 1, wherein said N,N'-disalicylidenediamine is at least one member selected from the group consisting of N,N'-disalicylidene $C_{2-8}$ alkylenediamines and N,N'-disalicylidene $C_{6-12}$ arylenediamines.

3. The oxidation process of claim 1, wherein said complex is shown by the following formula:

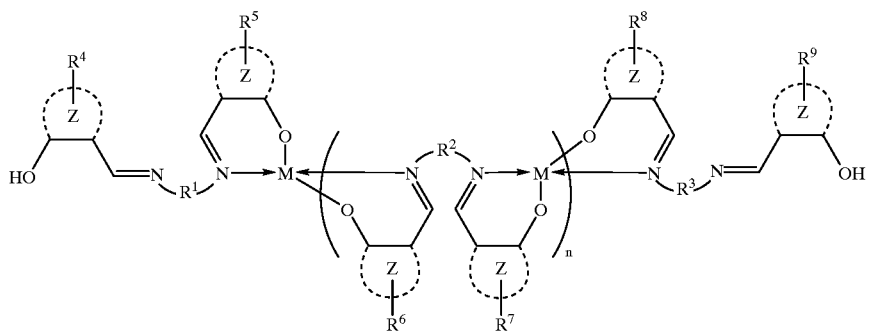

wherein $R^1$, $R^2$, and $R^3$ are the same or different and each represents an alkylene group, a cycloalkylene group, or an arylene group and may have a substituent; $R^4$ to $R^9$ are the same or different and each represents hydrogen atom, a halogen atom, an alkyl group, a hydroxyl group, a hydroxymethyl group, or an alkoxy group; each of the rings Z is an aromatic ring; M stands for manganese; and n is 0 or an integer of not less than 1.

4. The oxidation process of claim 1, wherein said complex is a complex of manganese having a valence of 2 to 4 with an N,N'-disalicylidene $C_{2-5}$ alkylenediamine.

5. The oxidation process of claim 1, wherein the melting point of said complex is 190 to 240° C.

6. The oxidation process of claim 1, wherein the melting point of said complex is 200 to 220° C.

7. A process according to claim 1, wherein the water content of a reaction system is not more than 1% by weight.

8. An oxidation process that comprises the step of oxidizing a substrate with oxygen in the presence of an oxidation catalyst comprising a crystalline complex of manganese with an N,N'-disalicylidenediamine and a basic nitrogen-containing compound, wherein said complex comprises m+1 moles of the N,N'-disalicylidenediamine coordinated to m moles of said manganese and m is an integer of not less than 1, and wherein the infrared spectrum of the complex indicates an absorption peak for the hydroxyl group.

9. The oxidation process of claim 8, wherein said nitrogen-containing compound is an alicyclic or aromatic cyclic base having a plurality of nitrogen atoms.

10. The oxidation process of claim 9, wherein the ring of said cyclic base contains at least one nitrogen atom.

11. The oxidation process of claim 9, wherein said cyclic base has 2 to 6 nitrogen atoms.

12. The oxidation process of claim 9, wherein said cyclic base is at least one member selected from the group consisting of 5- to 10-membered mono- and heterocyclic compounds, azabicyclo $C_{7-12}$ alkanes, azatricyclo $C_{8-16}$ alkanes, and aromatic heterocyclic compounds having (i) at least one nitrogen atom as a hetero atom, and (ii) an amino group or an N-substituted amino group or both.

13. The oxidation process of claim 8, wherein said nitrogen-containing compound is a tertiary amine.

14. The oxidation process of claim 8, wherein the proportion of said nitrogen-containing compound relative to said complex is 0.1/1 to 500/1 (molar ratio).

15. A process according to claim 8, wherein the water content of a reaction system is not more than 1% by weight.

16. A process for producing ketoisophorone or a derivative thereof, which comprises oxidizing β-isophorone or a derivative thereof with molecular oxygen in the presence of an oxidation catalyst comprising a crystalline complex of manganese with an N,N'-disalicylidenediamine and, optionally, a basic nitrogen-containing compound, wherein said complex comprises m+1 moles of the N,N'-disalicylidenediamine coordinated to m moles of said manganese and m is an integer of not less than 1, and wherein the infrared spectrum of the complex indicates an absorption peak for the hydroxyl group.

17. A process according to claim 16, wherein the amount of the complex is $1\times10^{-5}$ to $1\times10^{-2}$ mole relative to 1 mole of β-isophorone or a derivative thereof.

18. A process according to claim 16, wherein said oxidation is carried out in a ketone solvent.

* * * * *